United States Patent [19]

Paul et al.

[11] 4,124,766

[45] Nov. 7, 1978

[54] SUBSTITUTED 3-(4-IMIDAZOLYLMETHYLENE)CARBAZIC AND THIOCARBAZIC ACID ESTERS

[75] Inventors: Rolf Paul, River Vale, N.J.; Judith Menschik, Tappan, N.Y.

[73] Assignee: American Cyanamid Company, Stamford, Conn.

[21] Appl. No.: 848,836

[22] Filed: Nov. 7, 1977

Related U.S. Application Data

[63] Continuation-in-part of Ser. No. 765,317, Feb. 3, 1977, abandoned.

[51] Int. Cl.² ............................................. C07D 233/64
[52] U.S. Cl. .................................. 548/337; 424/247; 544/184; 548/342; 548/343; 548/351
[58] Field of Search .............................. 548/343, 337

[56] References Cited

U.S. PATENT DOCUMENTS

| 3,641,047 | 2/1972 | Beaman et al. | 548/338 |
| 3,686,203 | 8/1972 | Miller | 548/339 |
| 3,923,681 | 12/1975 | Warner | 252/300 |

OTHER PUBLICATIONS

Buechel et al., Chem. Abst. 1973, vol. 78, No. 97647n.
Korosi et al., Chem. Abst. 1970, vol. 72, No. 100334s.
Robba et al., Chem. Abst. 1975, vol. 83, No. 179008x.

*Primary Examiner*—Natalie Trousof
*Assistant Examiner*—Natalia Harkaway
*Attorney, Agent, or Firm*—Harry H. Kline

[57] ABSTRACT

There are provided substituted 3-(4-imidazolylmethylene)carbazic acid esters and 3-(4-imidazolylmethylene)dithiocarbazic acid esters useful as intermediates for the preparation of compounds which inhibit the enzyme cyclic-AMP phosphodiesterase.

10 Claims, No Drawings

SUBSTITUTED 3-(4-IMIDAZOLYLMETHYLENE)CARBAZIC AND THIOCARBAZIC ACID ESTERS

This application is a continuation-in-part of our copending application, Ser. No. 765,317, filed on Feb. 3, 1977, now abandoned.

BRIEF SUMMARY OF THE INVENTION

This invention relates to new organic compounds and, more particularly, is concerned with novel substituted 3-(4-imidazolylmethylene)carbazic and dithiocarbazic acid esters which may be represented by the following structural formula:

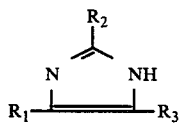

wherein $R_1$ is hydrogen, chloro, bromo or alkyl having up to 3 carbon atoms; $R_2$ is hydrogen, alkyl having up to 6 carbon atoms, cycloalkyl $C_3$-$C_6$, methoxymethyl, phenyl, naphthyl, benzyl or monosubstituted phenyl, wherein said latter mono-substituted substituent is alkyl $C_1$-$C_3$ alkoxy $C_1$-$C_3$, halo or nitro; and $R_3$ is a moiety of the formulae:

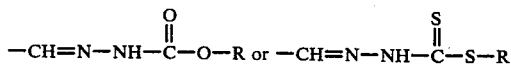

wherein R is alkyl having up to 3 carbon atoms. The novel compounds of the present invention may exist in two tautomeric forms which may be represented as follows and which are equivalent for purposes of this invention.

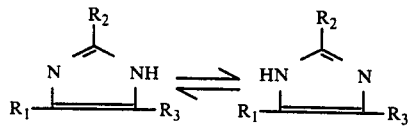

A preferred embodiment of the present invention may be represented by structural formula (I) wherein $R_1$ is hydrogen, chloro, bromo or methyl and $R_2$ is hydrogen, alkyl having up to 4 carbon atoms, cycloalkyl $C_3$-$C_6$, phenyl, m-tolyl, or benzyl.

DETAILED DESCRIPTION OF THE INVENTION

The novel compounds of the present invention are generally obtainable as white to yellow crystalline materials having characteristic melting points and absorption spectra and which may be purified by recrystallization from common organic solvents such as methanol, ethanol, dimethylformamide, chloroform, and the like. They are appreciably soluble in non-polar organic solvents such as diphenyl ether but are relatively insoluble in water.

The novel compounds of the present invention may be readily prepared in accordance with the following reaction scheme wherein is also set forth their conversion to the inhibitors of the enzyme phosphodiesterase:

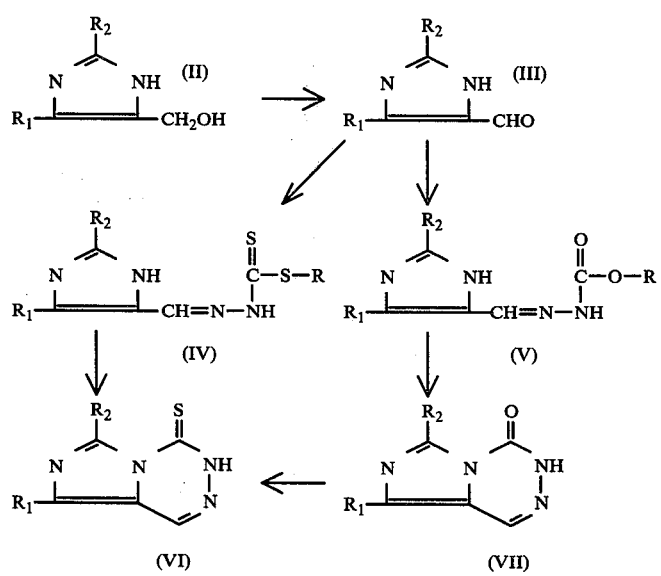

wherein R, $R_1$, and $R_2$ are as hereinabove defined. In accordance with the above reaction scheme, an appropriately substituted 4-imidazolemethanol (II) is oxidized with concentrated nitric acid to provide the corresponding 4-imidazolecarboxaldehyde (III). This oxidation is best carried out by suspending or dissolving each gram of starting material (II) in from about one ml. to about seven ml. of concentrated nitric acid and heating the reaction mixture at steam bath temperature for 2-3 hours. Alternatively, the reaction mixture may first be allowed to stand at room temperature for 8-16 hours and then heated for a short time (15-30 minutes) on the steam bath. The resulting reaction solution is preferably first diluted with water and then neutralized with any convenient base such as caustic, soda ash, or concentrated aqueous ammonia. The precipitated product (III) is removed, washed with water, and purified by recrystallization from common organic solvents such as ethyl acetate, ethanol, and the like. Alternatively, the 4-imidazolemethanol (II) may be oxidized with manganese dioxide in chloroform or tetrahydrofuran at the reflux temperature for a period of 4–6 hours to provide the 4-imidazolecarboxaldehyde (III).

The 4-imidazolecarboxaldehyde (III) may be readily converted to the 3-(4-imidazolylmethylene)dithiocarbazic acid ester (IV) or the 3-(4-imidazolylmethylene)-carbazic acid ester (V) by treatment with an alkyl dithiocarbazinate or with an alkyl carbazate, respectively. This condensation is conveniently carried out in a lower alkanol solvent containing a few drops of glacial acetic acid at a temperature of 25°–75° C. whereupon the product (IV) or (V) forms almost immediately and is removed by filtration. Typical compounds which may be so prepared are 3-[2,5-dimethyl-4-imidazolyl)methylene]carbazic acid methyl ester, 3-[(5-chloro-2-phenyl-4-imidazolyl)methylene]carbazic acid n-propyl ester, 3-[(2,5-diethyl-4-imidazolyl)methylene]dithiocarbazic acid ethyl ester, 3-[(5-isopropyl-2-isobutyl-4-imidazolyl)methylene]dithiocarbazic acid ethyl ester, and 3-[(5-chloro-2-phenyl-4-imidazolyl)methylene]dithiocarbazic acid isopropyl ester. Cyclization of the 3-(4-imidazolylmethylene)dithiocarbazic acid ester (IV) and the 3-(4-imidazolylmethylene)carbazic acid ester (V) is readily accomplished by heating in a non-polar high boiling organic solvent such as diphenyl ether at 175°–275° C. for 15–30 minutes whereby the corresponding imidazo[1,5-d]-as-triazine-4(3H)-thiones (VI) and imidazo[1,5-d]-as-triazin-4(3H)-ones (VII) are obtained.

The compounds (VII) wherein $R_1$ is chloro or bromo may be prepared by the chlorination of bromination, respectively, of the corresponding compounds (VII) wherein $R_1$ is hydrogen. This halogenation is accomplished by treating the starting materials with chlorine or bromine in an inert solvent such as chloroform or carbon tetrachloride at steam bath temperature. The oxo compounds (VII) can be converted to the thio compounds (VI) by treating with phosphorus pentasulfide in an inert solvent such as pyridine at the reflux temperature. This is a particularly convenient method when $R_1$ is halogen.

The products (VI) and (VII) are active in inhibiting the enzyme cyclic-AMP phosphodiesterase which is responsible for the metabolism of cyclic AMP. As such, they are useful in the treatment of psoriasis, a disease in which the epidermal cyclic AMP levels are reported to be decreased. Also as such, they are useful in the treatment of asthma, since elevated levels of cyclic AMP in most cells are reported to inhibit the release of histamine and other mediators and since elevated levels of cyclic AMP in bronchial smooth muscle are reported to cause bronchodilation. See Ann. Reports in Medicinal Chem., Vol. 10, 197 (1975).

The inhibition of phosphodiesterase is determined by the mouse skin and monkey lung phosphodiesterase (PDE) inhibition tests as follows:

(A) MOUSE SKIN INHIBITION

Preparation of Mouse Skin PDE

Hairless mice (Jackson Laboratories), 3–4 months old are killed by cervical dislocation and their skins removed. Epidermal slices are taken at a thickness of 0.2 mm. The slices are weighed and homogenized at 100 mg./ml. in ice-cold tris-HCl buffer (0.04M, pH 8, containing 0.005M $MgCl_2$). Homogenates are centrifuged at 17,000 × gravity for 30 minutes. The supernatants are divided into aliquots which are stored at −20° C.

Dilutions of the PDE are made with tris-HCl buffer just prior to use.

Anion Exchange Resin

AG1-X2 ®, 220–400 mesh (a polystyrene anionic exchange resin 8% cross linked from Bio-Rad Lab.) is washed with 0.5N HCl, 0.5N NaOH, 0.5N HCl and repeatedly with double distilled water to pH 5. The resin is allowed to settle and 2 volumes of water are added to one volume of settled resin.

Purification of $^3H$ Cyclic AMP $^3H$-Cyclic AMP (21 c/m mole, Schwarz-Mann Inc.) is purified by addition of 0.1 to 0.2 ml. of stock (in 50% ethanol) to 5 ml. of anion exchange resin and 0.4 ml. of tris-HCl buffer. The mixture is vortexed, centrifuged at 1200 × gravity for 5 minutes and the supernatant is discarded. The resin is washed in the same manner eight more times with two volumes of tris-HCl buffer. Resin bound $^3H$-cyclic AMP is eluted by two successive washings with 4 ml. of 0.025N HCl (resin pH = 2.0). After centrifugation, the pooled acid washes containing $^3H$-cyclic AMP are aliquoted and lyophilized. The material is stored dry at −20° C. and reconstituted with tris-HCl buffer just prior to use with a volume sufficient to give approximately 200,000 CPM/0.1 ml.

PDE Assay

PDE activity is measured by the method of W. J. Thompson and N. N. Appleman, Biochemistry 10, 311 (1971). Assays are conducted in 12 × 75 mm. polypropylene test tubes. The reaction mixture consists of $^3H$-cyclic AMP (200,000 CPM), unlabeled cyclic AMP, PDE (100 ug. protein) and test compounds which are prepared by dissolving the compounds in methanol at a concentration of 10 mg./ml. and then dilution in tris-HCl buffer. Final concentration of the test compounds in the incubation mixture is 10 ug./ml. The total volume of the incubation mixture is increased to 0.4 ml. with tris-HCl buffer containing 3.75 millimoles of 2-mercaptoethanol. The enzyme is incubated for 10 minutes at room temperature in the presence of the test compounds or buffer prior to the addition of the mixture of $^3H$-cyclic AMP and unlabeled cyclic AMP. Reactions are run at 30° C. for 15 minutes and then terminated by immersing in acetone-dry ice until frozen, followed by boiling for 3 minutes. Tubes are cooled to room temperature. $^3H$-5′ AMP, formed in the reaction is converted to $^3H$-adenosine by the addition of 0.1 ml. of a solution of 5′-nucleotidase [16 ug./ml. in double distilled water Crotalus venom (Sigma Chemicals)] to the tubes which are incubated for 20 minutes at room temperature. This reaction is ended by the addition of one ml. of ice cold, stirred resin slurry which binds charged nucleotides (including $^3H$-cyclic AMP) but not $^3H$-adenosine. Tubes are vortexed and immersed in an ice bath for 15 minutes and then centrifuged at 1200 × gravity for 5 minutes. A 0.5 ml. portion is taken from each, placed in liquid scintillation vials with 10 ml. of Ready-Solv VI (Beckman Ind.) and counted for radio activity. Assay "blanks," determined with assay buffer substituted for PDE are less than 1% of total $^3H$-cyclic AMP added when $^3H$-cyclic AMP is purified as indicated.

(B) MONKEY LUNG INHIBITION

Preparation of Monkey Lung Cyclic AMP Phosphodiesterase

Lung parenchyma of African green monkeys is homogenized in a Waring blender and centrifuged at 40,000 × gravity for 20 minutes. The supernatant is brought to 70% saturation of ammonium sulfate, centrifuged and the pellet redissolved and dialysed, before aliquoting and storage at −20° C.

Assay of Monkey Lung Phosphodiesterase

Phosphodiesterase is assayed by the method of Thompson and Appleman, ibid. An assay tube contains a 0.4 ml. solution of the following: 45 mM tris-HCl buffer, pH 7.4, 6.25 mM $MgCl_2$, 0.1 mM dithioerythritol, $10^{-6}$ M cyclic AMP, 0.1 uCi [$^3$H]-cyclic AMP, and test compound at the desired concentration (usually 1 mM or 0.1 mM). Compounds not readily soluble in water are dissolved at 40 times the desired concentration in methanol, and diluted 20 times with water. If the compound is not dissolved at this time, it is suspended by sonication before being diluted 1:2 into the assay tube. In this case the activity of the enzyme in the presence of the compound is compared to a solvent control (2.5% methanol), although the solvent alone has negligible effect. The reaction is initiated by addition of enzyme and proceeds at 25° C. for 20 minutes. It is terminated by incubation at 100° C. for 2 minutes. The tubes are cooled to 25° C., 0.8 ug of 5′-nucleotidase (Crotolus adamantus toxin) is added to each and the tubes incubated at 25° C. for 30 minutes. A one milliliter suspension of Bio-Rad Labs. AGIX8 ® (about 0.5 ml. of settled resin) is added, the tubes centrifuged at 900 × gravity for 10 minutes and an aliquot of supernatant removed for scintillation counting. The inhibition by the test compound is calculated as:

$$\% \text{ of control} = \frac{\text{'compound'} - \text{'blank'}}{\text{'control'} - \text{'blank'}}$$

where 'compound' is the cpm in the presence of compound, 'control' is the cpm in the absence of compound, and 'blank' is the cpm in the absence of enzyme. Since this assay requires sequential hydrolysis of cyclic AMP to AMP (by phosphodiesterase) followed by hydrolysis of AMP to adenosine (by 5′-nucleotidase), a compound which profoundly inhibited nucleotidase would appear to inhibit phosphodiesterase. For this reason, control tubes which contained [$^3$H]-AMP instead of [$^3$H]-cyclic AMP are run in parallel. A correction of the apparent phosphodiesterase activity is made for the rare compound which inhibited the hydrolysis of AMP.

Criterion for Activity as Inhibitor of Skin (A) or Lung (B) Phosphodiesterase A compound is considered active if it inhibits more than theophylline, that is, to 50% of control at 1 mM concentration of compound, or to 80% of control for 0.05 mM concentration of compound.

The results with typical compounds of formulae (VI) and (VII) on inhibition of phosphodiesterase are recorded in Table I below.

TABLE 1

| Compound | Mouse Lung Phosphodiesterase (B) | Mouse Skin Phosphodiesterase (A) |
|---|---|---|
| 6-Propyl-imidazo[1,5-d]-as-triazine-4(3H)-thione | Active | Active |
| 8-Methyl-6-phenyl-imidazo[1,5-d]-as-triazine-4(3H)-thione | | Active |
| 6-Phenyl-imidazo[1,5-d]-as-triazin-4(3H)-one | | Active |
| 8-Methyl-6-phneyl-imadazo[1,5-d]-as-triazin-4(3H)-one | Active | Active |
| 6-Propyl-imidazo[1,5-d]-as-triazin-4(3H)-one | | Active |
| 6,8-Dimethyl-imidazo[1,5-d]-as-triazin--4(3H)-one | Active | Active |
| 8-Bromo-6-phenyl-imidazo[1,5-d]-as-triazin-4(3H)-one | Active | Active |
| 8-Chloro-6-phenyl-imidazo[1,5-d]-as-triazin-4(3H)-one | Active | Active |
| 6-Benzyl-8-methyl-imidazo[1,5-d]-as-triazin-4(3H)-one | | Active |
| 6-tert-Butyl-8-methyl-imidazo[1,5-d]-as-triazin-4(3H)-one | Active | Active |
| 6-Benzyl-8-methyl-imidazo[1,5-d]-as-triazine-4(3H)-thione | Active | Active |
| 8-Methyl-6-propyl-imidazo[1,5-d]-as-triazine-4(3h)-thione | Active | Active |
| 8-Methyl-imidazo[1,5-d]-as-triazine-4(3H)-thione | | Active |
| 6-o-Propoxyphenyl-imidazo[1,5-d]-as-triazin-4(3H)-one | | Active |
| 6-Benzyl-imidazo[1,5-d]-as-triazin-4(3H)-one | | Active |
| 6-tert-Butyl-imidazo[1,5-d]-as-triazin-4(3H)-one | | Active |
| 8-Methyl-imidazo[1,5-d]-as-triazin-4(3H)-one | | Active |
| 6,8-Dimethyl-imidazo[1,5-d]-as-triazine-4(3H)-thione | | Active |

The invention will be described in greater detail in conjunction with the following specific examples.

EXAMPLE 1

5-Methyl-2-phenyl-4-imidazolemethanol

A 100 gm. portion of benzamidine hydrochloride is dissolved in a minimum of water (350 ml.) at room temperature. A 67 gm. portion of freshly distilled 2,3-butanedione is added giving a yellow solution. Adjusting the pH to 6-7 with 2N NaOH gives a solid which is allowed to stand at 0° C. for 2 hours, collected, pressed dry and then washed with 100 ml. of acetone. This material is heated with stirring on a steam bath with 855 ml. of concentrated HCl and 2437 ml. of water for 4 hours giving a solution. Cooling to room temperature overnight and then to 0° C. produces a solid which is collected and air dried. This solid is dissolved in 350 ml. of ethanol, filtered and cooled producing a gel, which is taken up in 250 ml. of 50°-60° C. water, adjusted to pH 5.5 with concentrated NaOH and then to pH 7-8 with solid $KHCO_3$. The mixture is cooled to 0° C. and the product is collected, washed with water, and air dried. This product is recrystallized from 1 liter of methanol giving the final product, m.p. 197°-199° C.

Alternatively, this product may be prepared by the method of Imbach et al., Bull. Soc. Chim. France, 1971, 1052.

EXAMPLE 2

2-Phenyl-4-imidazolemethanol

This product is prepared by the methods of Dziuron and Schunack, Arch. Pharm., 306, 347 (1973) and 307, 46 (1974).

EXAMPLE 3

2-n-Propyl-4-imidazolemethanol

A mixture of 180 gm. of 1,3-dihydroxyacetone dimer, 245 gm. of butyramidine hydrochloride and one liter of liquid ammonia are warmed to 60° C. for 5 hours in a bomb. The mixture is evaporated to dryness and the residue is stirred with 600 ml. of 2-propanol. The mixture is filtered and the filtrate is concentrated in vacuo. A 600 ml. portion of 50% saturated aqueous sodium carbonate is added and the mixture is extracted with three 150 ml. portions of tetrahydrofuran. The combined organic layers are washed with 330 ml. of saturated aqueous sodium carbonate. The organic layer is dried over anhydrous sodium sulfate and evaporated to dryness. The residue is twice recrystallized from acetone giving the product, m.p. 95°–101° C.

EXAMPLE 4

2,5-Dimethyl-4-imidazolemethanol hydrochloride

This product is prepared by the method of Imbach et al., Bull. Soc. Chim. France, 1971, 1052.

EXAMPLE 5

2-Methyl-4-imidazolemethanol

A 189 gm. portion of acetamidine hydrochloride and 180 gm. of 1,3-dihydroxyacetone are combined with 1 liter of liquid ammonia as described in Example 3, giving the desired product, m.p. 115°–117.5° C.

EXAMPLE 6

4,5-Dimethyl-2-n-propyl-2-imidazoline-4,5-diol hydrochloride

A 112.7 gm. portion of butyramidine hydrochloride is dissolved in 200 ml. of water. A 107 gm. portion of freshly distilled diacetyl is added and the mixture is stirred. The pH is adjusted to 6.5–7.0 with 2N NaOH and the solution is chilled. The desired product is collected as a solid, m.p. 104°–107° C.

EXAMPLE 7

5-Methyl-2-n-propyl-4-imidazolemethanol

The product from Example 6 is dissolved in 900 ml. of water and 350 ml. of concentrated hydrochloric acid, heated on a steam bath for 5 hours and then chilled. The solution is concentrated in vacuo and a mixture of 100 ml. of acetone and 100 ml. of ethanol is added. The mixture is filtered. The filtrate is evaporated and the residue is dissolved in 50 ml. of water and neutralized with a concentrated solution of $K_2CO_3$, until bubbling ceases. The top layer is separated and combined with 5 ml. of methanol. On standing, a precipitate forms. The solid is collected and the filtrate is diluted with acetone to give a second precipitate which is also collected. The solids are combined and recrystallized from hot acetone giving the desired product, m.p. 134°–136° C.

EXAMPLE 8

5-Methyl-4-imidazolemethanol

This product is prepared by the method of Ewins, J. Chem. Soc. 99, 2052 (1911).

EXAMPLE 9

2-(o-Propoxyphenyl)-4-imidazolemethanol

A 130 gm portion of salicylamide in 500 ml. of ethanol is reacted with 52.4 gm. of sodium methoxide and 164.9 gm. of 1-iodopropane by heating at reflux. The mixture is cooled, precipitated in 1500 ml. of water and the solid is recrystallized from hot ethanol giving o-propoxybenzamide.

A 109 gm. portion of the above compound in 500 ml. of chloroform is reacted with 49.4 ml. of methyl fluorosulfonate by refluxing for 3 hours. After cooling, the mixture is concentrated to an oil. Ether is added forming crystals which are recovered, giving o-propoxy benzimidic acid methyl ester fluorosulfate.

A 180 gm. portion of this latter product and 55.0 gm. of 1,3-dihydroxyacetone in one liter of liquid ammonia are reacted as in Example 3, giving the desired product, m.p. 90°–92° C.

EXAMPLE 10

2-Benzyl-4-imidazolemethanol

A 352 gm. portion of benzyl cyanide, 750 ml. of diethyl ether and 300 ml. of dry ethanol are placed in a 2 liter, three-necked flask with a magnetic stirrer, drying tube and quick-disconnect gas inlet. The mixture is stirred in an ice bath while hydrochloride gas is bubbled in for 1 hour. The mixture is placed in a chill room overnight. One liter of ether is added and the mixture is cooled. The precipitate is collected and washed with ether giving ethyliminophenylacetate hydrochloride.

A 272 gm. portion of the above compound and 126 gm. of 1,3-dihydroxyacetone in one liter of liquid ammonia are reacted as in Example 3 giving the desired product, m.p. 134°–135° C.

EXAMPLE 11

2-Methoxymethyl-4-imidazolemethanol

A 307.2 gm. portion of ethyl 2-methoxyacetimidate hydrochloride [Rule, J. Chem. Soc. 113, 9 (1918)] and 180 gm. of 1,3-dihydroxyacetone in one liter of liquid ammonia are reacted as described in Example 3 giving the desired product as an oil. A crystalline picrate salt (m.p. 175°–178° C.) is obtained by heating the oily product and picric acid in water.

EXAMPLE 12

2-tert-Butyl-4-imidazolemethanol

A mixture of 326 gm. of pivalimidic acid methyl ester hydrochloride and 193.5 gm. of 1,3-dihydroxyacetone in 2 liters of liquid ammonia are reacted as described in Example 3, giving the desired product, m.p. 212°–221° C.

EXAMPLE 13

2-tert-Butyl-5-methyl-4-imidazolemethanol

In a 2 liter, three-necked flask, equipped with a magnetic stirrer, drying tube and gas inlet tube, is put 200 gm. of trimethylacetonitrile, 250 ml. of methanol and 500 ml. of diethyl ether. Hydrochloride gas is bubbled in for 2 hours with stirring. The mixture is transferred to a beaker, ether is added and the beaker is covered and stored in a cold room overnight. A 500 ml. portion of ether is added and the solid is filtered and washed with ether, giving white crystals of pivalimidic acid methyl ester hydrochloride.

A 75 gm. portion of the above material is converted to methyl pivalimidate hydrochloride by the method of Brown and Evans, J. Chem. Soc. 1962, 4039.

A 61 gm. portion of this latter product is dissolved in 50 ml. of water with warming and then cooled to room temperature. A 38.3 gm. portion of freshly distilled diacetyl is added and the reaction is continued as described in Examples 6 and 7 giving the desired product as white crystals, m.p. 195.5°–196.5° C.

EXAMPLE 14

2-Benzyl-5-methyl-4-imidazolemethanol

To a solution of 109.6 gm. of -phenylacetamidine hydrochloride [Luckenbach, Chem. Ber. 17, 1423 (1884)] in 50 ml. of water is added 55.4 gm. of freshly distilled diacetyl. The mixture is stirred, the precipitate is collected, triturated in portions with 200 ml. of acetone and air dried, giving 2-benzyl-4,5-dimethyl-4,5-dihydroxyimidazolidine.

A mixture of 106 gm. of this latter product, 170 ml. of concentrated hydrochloride and 170 ml. of water is reacted as described in Example 7 giving the desired product, m.p. 134°–138° C.

EXAMPLE 15

2-Phenyl-4-imidazolecarboxaldehyde

A 17.4 gm. portion of 2-phenyl-4-imidazolemethanol and 13.4 ml. of concentrated $HNO_3$ are heated on a steam bath for 2½ hours. Three drops of fuming $HNO_3$ are added to star the reaction. The pH is adjusted to 8 with concentrated aqueous $Na_2CO_3$ and the mixture is cooled to 0° C. overnight. The solid is recovered, washed with water and recrystallized from a mixture of 70 ml. of ethyl acetate and 20 ml. of petroleum ether giving a yellow solid. Treatment of the mother liquor with petroleum ether gives an additional tacky substance which is triturated with 2-propanol giving a second solid. These two solids are taken up in hot 2-propanol and recrystallized as a yellow solid. This solid is recrystallized from ethanol:water (1:1) giving yellow crystals, m.p. 169°–171.5° C.

EXAMPLE 16

2-n-Propyl-4-imidazolecarboxaldehyde

A solution of 108.6 gm. of 2-n-propyl-4-imidazolemethanol in 107 ml. of concentrated $HNO_3$ is reacted as in Example 15, giving the desired product, m.p. 103.5°–105.5° C.

EXAMPLE 17

2-n-Butyl-4-imidazolecarboxaldehyde

Following the general procedure of Example 15, 2-n-butyl-4-imidazolemethanol is converted to 2-n-butyl-4-imidazolecarboxaldehyde.

EXAMPLE 18

5-Methyl-2-phenyl-4-imidazolecarboxaldehyde

A 102.1 gm. portion of 5-methyl-2-phenyl-4-imidazolemethanol is dissolved in 765 ml. of concentrated $HNO_3$. The solution is cooled in an ice bath and allowed to stand for 16 hours. The solution is heated on a steam bath for 30 minutes, diluted with 2.3 liters of water and neutralized with 50% NaOH while cooling in an ice bath. The solid is collected, dried, recrystallized from 200 ml. of ethanol and then from one liter of 1:2 ethanol:water giving the desired product, m.p. 102°–115° C.

Alternatively, this product may be prepared by the method of Diels and Schleich, Chem. Ber. 49, 1711 (1916).

EXAMPLE 19

5-Ethyl-2-phenyl-4-imidazolecarboxaldehyde

The procedure of Example 18 is repeated substituting an equimolecular amount of 5-ethyl-2-phenyl-4-imidazolemethanol for the 5-methyl-2-phenyl-4-imidazolemethanol employed in that example. There is thus obtained the title compound in equally good yield.

EXAMPLE 20

2,5-Dimethyl-4-imidazolecarboxaldehyde

A 42.2 gm. portion of 2,5-dimethyl-4-imidazolemethanol and 44.8 ml. of concentrated nitric acid are mixed. When the initial reaction subsides, the solution is heated on a steam bath for one hour. The reaction mixture is neutralized with concentrated aqueous sodium carbonate, then concentrated under vacuum. After leaching the residue with 150 ml. of hot ethanol several times, the combined organic solutions are concentrated under vacuum. Chromatographing the residual oil on silica gel gives a solid which is recrystallized from isopropanol-ethyl acetate to give the desired product, m.p. 164.5°–166° C.

EXAMPLE 21

5-Methyl-4-imidazolecarboxaldehyde

This product is prepared by the method of Hubball and Pyman, J. Chem. Soc. 1928, 21.

EXAMPLE 22

2-o-Propoxyphenyl-4-imidazolecarboxaldehyde

A 44 gm. portion of 2-(o-propoxyphenyl)-4-imidazolemethanol is placed in a 2 liter round bottom flask together with 500 ml. of chloroform and 100 gm. of manganese dioxide. The mixture is stirred and refluxed for 5½ hours. The reaction mixture is filtered while hot. The manganese dioxide is triturated with 500 ml. of hot chloroform and filtered. The two filtrates are combined and evaporated. The solid residue is recrystallized from 200 ml. of hot ethyl acetate and charcoal giving the desired product, m.p. 104°–105° C.

EXAMPLE 23

2-Methyl-4-imidazolecarboxaldehyde

A 143.0 ml. portion of concentrated $HNO_3$ is added in two portions to 119.2 gm. of 2-methyl-4-imidazolemethanol, with cooling after the first portion, and reacted as described in Example 15, giving the desired product, m.p. 170°–176° C.

Alternatively, this product may be made by the methods of Streith et al., Bull. Soc. Chim. France, 4159 (1971) and also Abushanab et al., J. Org. Chem. 40, 3376 (1975).

EXAMPLE 24

2-Benzyl-4-imidazolecarboxaldehyde

A 125 gm. portion of 2-benzyl-4-imidazolemethanol and 500 g. of manganese dioxide in 2 liters of chloroform are reacted as described in Example 22 giving the desired product, m.p. 130°–136° C.

EXAMPLE 25

2-(Methoxymethyl)-4-imidazolecarboxaldehyde

A 145.9 gm. portion of 2-methoxymethyl-4-imidazolemethanol and 137 ml. of concentrated HNO$_3$ are reacted as described in Example 15. After adjusting the pH to 7.0 with concentrated aqueous Na$_2$CO$_3$, the solution is concentrated under vacuum. Extraction of the residue three times with hot ethanol gives, after combining and concentrating the extracts, a yellow gum. This gum is chromatographed on silica gel. Fractions 7-15 are combined and recrystallized from 120 ml. of 2-propanol, treated with charcoal and the desired product is recovered, m.p. 100°-103° C.

EXAMPLE 26

2-Benzyl-5-methyl-4-imidazolecarboxaldehyde

A mixture of 8.79 gm. of 2-benzyl-5-methyl-4-imidazolemethanol and 55.7 ml. of concentrated HNO$_3$ are left at room temperature overnight. The solution is heated for 45 minutes on a steam bath, cooled, then basified with aqueous sodium carbonate. After heating the resulting mixture on a steam bath, it is cooled and the solid collected. Two recrystallizations from ethanol give the desired product, m.p. 171°-173° C.

EXAMPLE 27

2-Benzyl-5-n-propyl-4-imidazolecarboxaldehyde

The general procedure of Example 26 is repeated but replacing the 2-benzyl-5-methyl-4-imidazolemethanol employed in that example with 2-benzyl-5-n-propyl-4-imidazolemethanol.

EXAMPLE 28

5-Methyl-2-n-propyl-4-imidazolecarboxaldehyde

An 80 gm. portion of 5-methyl-2-n-propyl-4-imidazolemethanol is oxidized with 67.3 ml. of concentrated HNO$_3$. A second portion of 101.4 gm. of the above compound is oxidized with 77 ml. of the acid. The reaction mixtures are combined, neutralized and worked up as in Example 25, giving the desired product, m.p. 126°-129° C.

EXAMPLE 29

2-tert-Butyl-4-imidazolecarboxaldehyde

A 7.7 gm. portion of 2-tert-butyl-4-imidazolemethanol is added to 100 ml. of chloroform and 100 ml. of tetrahydrofuran and heated gently. A 25 gm. portion of manganese dioxide is added and the mixture is reacted as described in Example 22 giving the desired product as white crystals, m.p. 194°-195° C.

EXAMPLE 30

2-tert-Butyl-5-methyl-4-imidazolecarboxaldehyde

A 19.76 gm. portion of 2-tert-butyl-5-methyl-4-imidazolemethanol and 16.5 ml. of concentrated HNO$_3$ are reacted as described in Example 25 giving the desired product, m.p. 196°-198° C.

EXAMPLE 31

2-Isobutyl-5-isopropyl-4-imidazolecarboxaldehyde

The procedure of Example 30 is repeated substituting an equimolecular amount of 2-isobutyl-5-isopropyl-4-imidazolemethanol for the 2-tert-butyl-5-methyl-4-imidazolemethanol employed in that example. There is thus obtained the title compound in equally good yield.

EXAMPLE 32

3-(4-Imidazolylmethylene)dithiocarbazic acid methyl ester.

A 17.78 gm. portion of imidazole-4-carboxaldehyde (Pyman, J. Chem. Soc. 1916, 186) is dissolved in 200 ml. of hot ethanol. A hot solution of 24.4 gm. of methyl dithiocarbazinate [Audrieth et al., J. Org. Chem. 19, 733 (1954)] in 50 ml. of ethanol is added. A precipitate forms immediately and the mixture is heated and stirred for about 10 minutes. The mixture is cooled to 0° C. The precipitate is collected giving yellow crystals, m.p. 259°-261° C.

EXAMPLE 33

3-(2-Phenyl-4-imidazolylmethylene)dithiocarbazic acid methyl ester

A 35 gm. portion of 2-phenyl-4-imidazolecarboxaldehyde is taken up in 250 ml. of hot ethanol. A solution of 22.8 gm. of methyl dithiocarbazinate in 40 ml. of hot ethanol is added and the procedure of Example 32 is followed giving the desired product, m.p. 166°-170° C.

EXAMPLE 34

3-[(5-Methyl-2-phenyl-4-imidazolyl)methylene]dithiocarbazic acid methyl ester

A 60 gm. portion of 5-methyl-2-phenyl-4-imidazolecarboxaldehyde and 36.8 gm. of methyl dithiocarbazinate are reacted as described in Example 32 giving the desired product, m.p. 180°-185° C.

EXAMPLE 35

3-[(5-Ethyl-2-phenyl-4-imidazolyl)methylene]dithiocarbazic acid methyl ester

Following the general procedure of Example 34, 5-ethyl-2-phenyl-4-imidazolecarboxaldehyde is converted to 3-[(5-ethyl-2-phenyl-4-imidazolyl)methylene]-dithiocarbazic acid methyl ester.

EXAMPLE 36

3-(2-n-Propyl-4-imidazolylmethylene)dithiocarbazic acid methyl ester

A 60 gm. portion of 2-n-propyl-4-imidazolecarboxaldehyde and 53.7 gm. of methyl dithiocarbazinate are reacted as described in Example 32 giving the desired product, m.p. 95°-104° C.

EXAMPLE 37

3-(2-Methyl-4-imidazolyl-methylene)dithiocarbazic acid methyl ester

A 33 gm. portion of 2-methyl-4-imidazolecarboxaldehyde and 40.3 gm. of methyl dithiocarbazinate are reacted as described in Example 32 giving the desired product, m.p. 274°-279° C.

EXAMPLE 38

3-(5-Methyl-4-imidazolylmethylene)dithiocarbazic acid methyl ester

A 16 gm. portion of 5-methyl-4-imidazolecarboxaldehyde and 19.5 gm. of methyl dithiocarbazinate are reacted as described in Example 32 giving the desired product, m.p. 180°d resolidifies 230°-260° C.

EXAMPLE 39

3-[(2,5-Dimethyl-4-imidazolyl)methylene]dithiocarbazic acid methyl ester

A 20 gm. portion of 2,5-dimethyl-4-imidazolecarboxaldehyde and 20.8 gm. of methyl dithiocarbazinate are reacted as described in Example 32 giving the desired product, m.p. 279°–281° C.

EXAMPLE 40

3-{[2-(Methoxymethyl)-4-imidazolyl]methylene}dithiocarbazic acid methyl ester

A 40 gm. portion of 2-(methoxymethyl)-4-imidazolecarboxaldehyde and 38.4 gm. of methyl dithiocarbazinate are reacted as described in Example 32 giving the desired product, m.p. 150°–154° C.

EXAMPLE 41

3-[(5-Methyl-2-n-propyl-4-imidazolyl)methylene]dithiocarbazic acid methyl ester

A 20 gm. portion of 5-methyl-2-n-propyl-4-imidazolecarboxaldehyde and 17.7 gm. of methyl dithiocarbazinate are reacted as described in Example 32 giving the desired product, m.p. 175°–179° C.

EXAMPLE 42

3-[(2-benzyl-5-n-Propyl-4-imidazolyl)methylene]dithiocarbazic acid methyl ester

The general procedure of Example 41 is repeated but replacing the 5-methyl-2-n-propyl-4-imidazolecarboxaldehyde employed in that example with 2-benzyl-5-n-propyl-4-imidazolecarboxaldehyde.

EXAMPLE 43

3-[(2,5-Dimethyl-4-imidazolyl)methylene]carbazic acid ethyl ester

A 6.2 gm. portion of 2,5-dimethyl-4-imidazolecarboxaldehyde and 6.24 gm. of ethyl carbazate are reacted as described in Example 32 giving the desired product, m.p. 207.5°–210° C. (resolidifies 248°–252° C.).

EXAMPLE 44

3-(2-n-Propyl-4-imidazolylmethylene)carbazic acid ethyl ester

A 7.8 gm. portion of 2-n-propyl-4-imidazolecarboxaldehyde and 6.24 gm. of ethyl carbazate is reacted as described in Example 32 giving the desired product, m.p. 180°–182° C.

EXAMPLE 45

3-(2-Phenyl-4-imidazolylmethylene)carbazic acid ethyl ester

A mixture of 8.16 gm. of 2-phenyl-4-imidazolecarboxaldehyde and 5.52 gm. of ethyl carbazate are reacted as described in Example 32 giving the desired product, m.p. 196°–200° C.

EXAMPLE 46

3-[(5-Methyl-2-phenyl-4-imidazolyl)methylene]carbazic acid ethyl ester

A mixture of 10.25 gm. of 5-methyl-2-phenyl-4-imidazolecarboxaldehyde and 5.72 gm. of ethyl carbazate in 30 ml. of ethanol containing one drop of acetic acid is boiled for 30 minutes. The mixture is cooled to 0° C. and concentrated under an air stream on a steam bath. A 50 ml. portion of carbon tetrachloride is added and the mixture is cooled to 0° C. overnight. The solid is collected giving the desired product, m.p. 209°–211° C.

EXAMPLE 47

3-[(2-o-Propoxyphenyl-4-imidazolyl)methylene]carbazic acid ethyl ester

A 4.3 gm. portion of 2-o-propoxyphenyl-4-imidazolecarboxaldehyde and 1.98 gm. of ethyl carbazate are reacted as described in Example 32 giving the desired product, m.p. 129°–132° C.

EXAMPLE 48

3-[(2-Benzyl-4-imidazolyl)methylene]carbazic acid ethyl ester

To a 37.2 gm. portion of 2-benzyl-4-imidazolecarboxaldehyde in 200 ml. of ethanol is added 20.8 gm. of ethyl carbazate and a few drops of concentrated acetic acid. The mixture is reacted as described in Example 32 giving the desired product m.p. 184°–185° C.

EXAMPLE 49

3-(2-tert-Butyl-4-imidazolylmethylene)carbazic acid ethyl ester

A 7.6 gm. portion of 2-tert-butyl-4-imidazolecarboxaldehyde and 5.2 gm. of ethyl carbazate in 100 ml. of ethanol are reacted as described in Example 32 giving the desired product, m.p. 194°–197° C.

EXAMPLE 50

3-(2-n-Butyl-4-imidazolylmethylene)carbazic acid ethyl ester

The procedure of Example 49 is repeated substituting an equimolecular amount of 2-n-butyl-4-imidazolecarboxaldehyde for the 2-tert-butyl-4-imidazolecarboxaldehyde employed in that example. There is thus obtained the title compound in equally good yield.

EXAMPLE 51

3-(2-Methyl-4-imidazolylmethylene)carbazic acid ethyl ester

A solution of 16.68 gm. of ethyl carbazate in 50 ml. of hot ethanol is added to a solution of 16.50 gm. of 2-methyl-4-imidazolecarboxaldehyde in 100 ml. of hot ethanol containing 2 drops of acetic acid. The reaction is carried out as described in Example 32 giving the desired product, m.p. 210.5°–211.5° C.

EXAMPLE 52

3-(5-Methyl-4-imidazolylmethylene)carbazic acid ethyl ester

A mixture of 7.0 gm. of 5-methyl-4-imidazolecarboxaldehyde and 7.3 gm. of ethyl carbazate are reacted as described in Example 32 giving the desired product, m.p. 195°–203° C.

EXAMPLE 53

3-{[2-(Methoxymethyl)-4-imidazolyl]methylene)carbazic acid ethyl ester

A 19.60 gm. portion of 2-(methoxymethyl)-4-imidazolecarboxaldehyde and 16.02 gm. of ethyl carbazate are reacted as described in Example 32 giving the desired product, m.p. 186°–190° C.

EXAMPLE 54

3-[(2-Benzyl-5-methyl-4-imidazolyl)methylene]carbazic acid ethyl ester

A 4.08 gm. portion of 2-benzyl-5-methyl-4-imidazolecarboxaldehyde and 2.29 gm. of ethyl carbazate are reacted as described in Example 32 giving the desired product, m.p. 190°–191.5° C.

EXAMPLE 55

3-[(2-tert-Butyl-5-methyl-4-imidazolyl)methylene]carbazic acid ethyl ester

A 6.17 gm. portion of 2-tert-butyl-5-methyl-4-imidazolecarboxaldehyde and 4.20 gm. of ethyl carbazate are reacted as described in Example 32 giving the desired product, m.p. 226°–228.5° C.

EXAMPLE 56

3-[(2-Isobutyl-5-isopropyl-4-imidazolyl)methylene]carbazic acid ethyl ester

Following the general procedure of Example 55, 2-isobutyl-5-isopropyl-4-imidazolecarboxaldehyde is converted to the title compound in equally good yield.

EXAMPLE 57

3-[(5-Methyl-2-n-propyl-4-imidazolyl)methylene]carbazic acid ethyl ester

A 12 gm. portion of 5-methyl-2-n-propyl-4-imidazolecarboxaldehyde and 9.06 gm. of ethyl carbazate are reacted as described in Example 32 giving the desired product, m.p. 184°–188° C.

EXAMPLE 58

Imidazo[1,5-d]-as-triazine-4-(3H)-thione

A suspension of 164.5 gm. of 3-(4-imidazolylmethylene)dithiocarbazic acid methyl ester in 1.2 liters of diphenyl ether is heated and stirred at 175° C. until the methylmercaptan evolution subsides (20 minutes). The precipitate obtained on cooling to room temperature is collected and washed with petroleum ether, then acetone. The precipitate is then slurried with 1.2 liters of boiling methanol and filtered while hot to give the desired product, m.p. 271°–273° C.

EXAMPLE 59

8-Methyl-imidazo[1,5-d]-as-triazine-4(3H)-thione

A suspension of 14.39 gm. of 3-(5-methyl-4-imidazolylmethylene)dithiocarbazic acid methyl ester in 100 ml. of diphenyl ether is reacted as described in Example 58 giving the desired product as yellow crystals, m.p. 262°–268° C.

EXAMPLE 60

6-Phenyl-imidazo[1,5-d]-as-triazine-4(3H)-thione

A suspension of 7.05 gm. of 3-(2-phenyl-4-imidazolylmethylene)dithiocarbazic acid methyl ester in 100 ml. of diphenyl ether is reacted as described in Example 58 giving the desired product, m.p. 210° C.

EXAMPLE 61

6-n-Propyl-imidazo[1,5-d]-as-triazine-4(3H)-thione

A 102.2 gm. portion of 3-(2-n-propyl-4-imidazolylmethylene)dithiocarbazic acid methyl ester in 500 ml. of diphenyl ether is reacted as described in Example 58 giving the desired product as a white solid, m.p. 201.5°–203.5° C.

EXAMPLE 62

8-Methyl-6-phenyl-imidazo[1,5-d]-as-triazine-4(3H)-thione

A mixture of 73.4 gm. of 3-[(5-methyl-2-phenyl-4-imidazolyl)methylene]dithiocarbazic acid methyl ester and 500 ml. of diphenyl ether is reacted as described in Example 58 giving the desired product as purple crystals, m.p. 237.5°–239° C.

EXAMPLE 63

8-Ethyl-6-phenyl-imidazo[1,5-d]-as-triazine-4(3H)-thione

The general procedure of Example 62 is repeated but replacing the 3-[(5-methyl-2-phenyl-4-imidazolyl)methylene]dithiocarbazic acid methyl ester employed in that example with 3-[(5-ethyl-2-phenyl-4-imidazolyl)methylene]dithiocarbazic acid methyl ester.

EXAMPLE 64

6,8-Dimethyl-imidazo[1,5-d]-as-triazine-4(3H)-thione

A mixture of 30.26 gm. of 3-[(2,5-dimethyl-4-imidazolyl)methylene]dithiocarbazic acid methyl ester and 125 ml. of diphenyl ether is reacted as described in Example 58 giving a solid which is the desired product, m.p. 287.5°–290° C.

EXAMPLE 65

6-Benzyl-8-methyl-imidazo[1,5-d]-as-triazine-4(3H)-thione

A 2.04 gm. portion of 2-benzyl-5-methyl-4-imidazolecarboxaldehyde is dissolved in 20 ml. of ethanol containing 2 drops of acetic acid. A 1.34 gm. portion of methyldithiocarbazinate is added, the mixture is boiled for 30 minutes and then cooled to 0° C. overnight. The mixture is evaporated giving 3-[(2-benzyl-5-methylimidazoyl)methylene]dithiocarbazic acid methyl ester as an oil.

A 3.40 gm. portion of the above product is dissolved in 30 ml. of diphenyl ether and heated for 9 minutes at 194°–207° C. The mixture is cooled to room temperature and diluted with hexane. The solid is recrystallized from 150 ml. of methanol and treated with charcoal giving the desired product, m.p. 207°–209.5° C.

EXAMPLE 66

6-Benzyl-8-n-propyl-imidazo[1,5-d]-as-triazine-4(3H)-thione

The procedure of Example 65 is repeated substituting an equimolecular amount of 3-[(2-benzyl-5-n-propylimidazolyl)methylene]dithiocarbazic acid methyl ester for the 3-[(2-benzyl-5-methylimidazolyl)methylene]dithiocarbazic acid methyl ester employed in that example. There is thus obtained the title compound in equally good yield.

EXAMPLE 67

8-Methyl-6-n-propyl-imidazo[1,5-d]-as-triazine-4(3H)-thione

A mixture of 32.12 gm. of 3-[(5-methyl-2-n-propyl-4-imidazolyl)methylene]dithiocarbazic acid methyl ester and 200 ml. of diphenyl ether is reacted as described in

EXAMPLE 68

6-Methyl-imidazo[1,5-d]-as-triazine-4(3H)-thione

A mixture of 53.9 gm. of 3-(2-methyl-4-imidazolylmethylene)dithiocarbazic acid methyl ester and 200 ml. of diphenyl ether is reacted as described in Example 58 giving the desired product, m.p. 280.5°–284° C.

EXAMPLE 69

6-Methoxymethyl-imidazo[1,5-d]-as-triazine-4(3H)-thione

A mixture of 62.4 gm. of 3-{[2-(methoxymethyl)-4-imidazolyl]methylene}dithiocarbazic acid methyl ester and 250 ml. of diphenyl ether is reacted as described in Example 58 giving the desired product, m.p. 219.5°–223° C.

EXAMPLE 70

6-o-Propoxyphenyl-imidazo[1,5-d]-as-triazin-4(3H)-one

A 10.5 gm. portion of 3-[(2-o-propoxyphenyl-4-imidazolyl)methylene]carbazic acid ethyl ester in 100 ml. of diphenyl ether is heated on an oil bath with stirring at 255°–265° C. until effervesence subsides. The mixture is cooled to room temperature. The addition of petroleum ether produces a solid which is recrystallized from methanol with the aid of charcoal giving the desired product as a bright yellow solid, m.p. 197°–200° C.

EXAMPLE 71

6-Benzyl-imidazo[1,5-d]-as-triazin-4(3H)-one

A 7.0 gm. portion of 3-[(2-benzyl-4-imidazolyl)methylene]carbazic acid ethyl ester in 50 ml. of diphenyl ether is reacted as described in Example 70 giving the desired product as white crystals, m.p. 215°–217° C.

EXAMPLE 72

6-Phenyl-imidazo[1,5-d]-as-triazin-4(3H)-one

A 7.76 gm. portion of 3-(2-phenyl-4-imidazolylmethylene)carbazic acid ethyl ester in 50 ml. of diphenyl ether is reacted as described in Example 70 giving the desired product, m.p. 245°–248° C.

EXAMPLE 73

8-Methyl-6-phenyl-imidazo[1,5-d]-as-triazin-4(3H)-one

An 8.33 gm. portion of 3-[(5-methyl-2-phenyl-4-imidazolyl)methylene]carbazic acid ethyl ester in 60 ml. of diphenyl ether is heated in an oil bath at 215°–230° C. for 20 minutes. The reaction mixture is diluted to 400 ml. with petroleum ether. The precipitate is collected and recrystallized from 350 ml. of benzene giving the desired product, m.p. 182°–184.5° C.

EXAMPLE 74

6-n-Propyl-imidazo[1,5-d]-as-triazin-4(3H)-one

An 8.75 gm. portion of 3-(2-n-propyl-4-imidazolylmethylene)carbazic acid ethyl ester in 50 ml. of diphenyl ether is reacted as described in Example 70 giving the desired product, m.p. 159°–162.5° C.

EXAMPLE 75

6,8-Dimethyl-imidazo[1,5-d]-as-triazin-4(3H)-one

A mixture of 7.37 gm. of 3-[(2,5-dimethyl-4-imidazoly)methylene]carbazic acid ethyl ester and 50 ml. of diphenyl ether is reacted as described in Example 70 giving the desired product, m.p. 263°–263.5° C.

EXAMPLE 76

6-tert-Butyl-imidazo[1,5-d]-as-triazin-4(3H)-one

A 6.15 gm. portion of 3-(2-tert-butyl-4-imidazolylmethylene)carbazic acid ethyl ester in 40 ml. of diphenyl ether is reacted as described in Example 70 giving the desired product, m.p. 186°–188° C.

EXAMPLE 77

6-n-Butyl-imidazo[1,5-d]-as-triazin-4(3H)-one

Following the general procedure of Example 76, 3-(2-n-butyl-4-imidazolylmethylene)carbazic acid ethyl ester is converted to the title compound.

EXAMPLE 78

6-Methyl-imidazo[1,5-d]-as-triazin-4(3H)-one

A 27.2 gm. portion of 3-(2-methyl-4-imidazolylmethylene)carbazic acid ethyl ester in 200 ml. of diphenyl ether is reacted as described in Example 70 giving the desired product, m.p. 303°–305.5° C.

EXAMPLE 79

8-Methyl-imidazo[1,5-d]-as-triazin-4(3H)-one

A mixture of 10.26 gm. of 3-(5-methyl-4-imidazolylmethylene)carbazic acid ethyl ester and 100 ml. of diphenyl ether is reacted as described in Example 70 giving the desired product, m.p. 276°–282° C.

EXAMPLE 80

6-Benzyl-8-methyl-imidazo[1,5-d]-as-triazin-4(3H)-one

A mixture of 4.89 gm. of 3-[(2-benzyl-5-methyl-4-imidazolyl)methylene]carbazic acid ethyl ester and 50 ml. of diphenyl ether is reacted as described in Example 70 giving the desired product, m.p. 244°–247° C.

EXAMPLE 81

6-tert-Butyl-8-methyl-imidazo[1,5-d]-as-triazin-4(3H)-one

A mixture of 5.11 gm. of 3-[(2-tert-butyl-5-methyl-4-imidazolyl)methylene]carbazic acid ethyl ester and 50 ml. of diphenyl ether is reacted as described in Example 70 giving the desired product, m.p. 198°–200° C.

EXAMPLE 82

6-Isobutyl-8-isopropyl-imidazo[1,5-d]-as-triazin-4(3H)-one

The general procedure of Example 81 is repeated but replacing the 3-[(2-tert-butyl-5-methyl-4-imidazolyl)methylene]carbazic acid ethyl ester employed in that example with 3-[(2-isobutyl-5-isopropyl-4-imiazolyl)methylene]carbazic acid ethyl ester.

EXAMPLE 83

8-Methyl-6-n-propyl-imidazo[1,5-d]-as-triazin-4(3H)-one

A 14.50 gm. portion of 3-[(5-methyl-2-n-propyl-4-imidazolyl)methylene]carbazic acid ethyl ester and 100 ml. of diphenyl ether are reacted as described in Example 70 giving the desired product, m.p. 129.5°–131.5° C.

EXAMPLE 84

6-Methoxymethyl-imidazo[1,5-d]-as-triazin-4(3H)-one

A mixture of 25.9 gm. of 3-{[2-(methoxymethyl)-4-imidazolyl]methylene}carbazic acid ethyl ester and 125 ml. of diphenyl ether is reacted as described in Example 70 giving the desired product, m.p. 200°–205° C.

EXAMPLE 85

8-Bromo-6-phenyl-imidazo[1,5-d]-as-triazin-4(3H)-one

A 3.0 gm. portion of 6-phenyl-imidazo[1,5-d]-as-triazin-4(3H)-one is stirred with 100 ml. of chloroform. The mixture is heated slightly and a solution of 1 ml. of bromine in 10 ml. of chloroform is slowly dripped into the reaction mixture. The mixture is refluxed for one hour, cooled to room temperature, and filtered. To the solid is added aqueous $Na_2CO_3$ and chloroform and the mixture is shaken in a separatory funnel. The remaining solid and the organic phase are combined and evaporated on a steam bath. Methanol and 2-propanol are added and the mixture is treated twice with charcoal. Cooling gives the desired product as a solid, m.p. 192°–194° C.

EXAMPLE 86

8-Bromo-6-n-butyl-imidazo[1,5-d]-as-triazin-4(3H)-one

The procedure of Example 85 is repeated substituting an equimolecular amount of 6-n-butyl-imidazo[1,5-d]-as-triazin-4(3H)-one for the 6-phenyl-imidazo[1,5-d]-as-triazin-4(3H)-one employed in that example. There is thus obtained the title compound in equally good yield.

EXAMPLE 87

8-Chloro-6-phenyl-imidazo[1,5-d]-as-triazin-4(3H)-one

A 5.0 gm. pportion of 6-phenyl-imidazo[1,5-d]-as-triazin-4(3H)-one is mixed with 100 ml. of chloroform on a steam bath while chlorine gas is bubbled through the mixture. A 25 ml. portion of methanol is added. Chlorine is again bubbled through for 10–15 minutes. The mixture is cooled to room temperature, transferred to a separatory funnel, washed with aqueous $Na_2CO_3$, aqueous $NaHSO_3$ and finally with water. The mixture is evaporated to 75 ml. on a steam bath, cooled and filtered. The filtrate is evaporated overnight giving a solid. This solid is dissolved in 30 ml. of hot chloroform and filtered. The filtrate is treated with charcoal and 2-propanol is added giving the desired product as a solid, m.p. 201°–203° C.

EXAMPLE 88

8-Chloro-6-benzyl-imidazo[1,5-d]-as-triazin-4(3H)-one

Following the general procedure of Example 87, 6-benzyl-imidazo[1,5-d]-as-triazin-4(3H)-one is chlorinated to give the title compound.

EXAMPLE 89

3-[(5-Chloro-2-phenyl-4-imidazolyl)methylene]dithiocarbazic acid methyl ester

Following the general procedure of Example 34, 5-chloro-2-phenyl-4-imidazolecarboxaldehyde is converted to the title compound in equally good yield.

EXAMPLE 90

8-Chloro-6-phenyl-imidazo[1,5-d]-as-triazine-4(3H)-thione

The general procedure of Example 62 is repeated but replacing the 3-[(5-methyl-2-phenyl-4-imidazolyl)methylene]dithiocarbazic acid methyl ester employed in that example with 3-[(5-chloro-2-phenyl-4-imidazolyl)methylene]dithiocarbazic acid methyl ester.

EXAMPLE 91

8-Bromo-6-phenyl-imidazo[1,5-d]-as-triazine-4(3H)-thione

To a solution of 8-bromo-6-phenyl-imidazo[1,5-d]-as-triazin-4(3H)-one (5 gm.) in pyridine (100 ml.) is added phosphorus pentasulfide (5 gm.). The mixture is heated at 100° C. for 6 hours, cooled, and the product isolated by filtration and then washed with dilute hydrochloric acid.

EXAMPLE 92

General methods for the preparation of 3-[(2-substituted-5-methyl-4-imidazolyl)methylene]carbazic acid methyl esters A 3-[(5-methyl-2-m-tolyl-4-imidazolyl)methylene]carbazic acid, methyl ester.

A mixture of 5-methyl-2-m-tolyl-4-imidazolecarboxaldehyde (6.9 gm., 0.034 mole), methyl carbazate (3.1 gm., 0.034 mole), methylene chloride (70 ml.) and acetic acid (1 drop) is refluxed for 1 hour. The precipitated white solid is collected by filtration to yield 7.1 gm. (0.026 mole), m.p. 162°–164° C.

By the above procedure several 2-aryl analogs of the compound are prepared. These compounds, their melting points and analyses are listed in Table V below.

B Preparation of 3-[(2-alkyl or cycloalkyl-5-methyl-4-imidazolyl)methylene]carbazic acid, methyl esters.

A mixture of 2-alkyl(cycloalkyl)-5-methylimidazole-4-carboxaldehyde (0.1 mole), methyl carbazate (0.1 mole), toluene (60 ml.) and acetic acid (0.5 ml.) is refluxed for 2 hours. The reaction mixture is then cooled down, the solids are collected by filtration, and are recrystallized from the appropriate solvent.

The 2-alkyl and cycloalkyl compounds prepared by the above procedure are listed in Table II below.

TABLE II $$\begin{array}{c} H \\ | \\ N \\ R_2 \!-\!\! \Big\langle \quad \quad \text{CH}=\text{N}-\text{NH}-\text{CO}_2\text{CH}_3 \\ N \!-\! R_1 \end{array}$$

| $R_2$ | $R_1$ | m.p.(° C) | Analysis Calculated | Found |
|---|---|---|---|---|
| $O_2N-\bigcirc-$ | $CH_3$ | 264–265(d) | C 51.49<br>H 4.32<br>N 23.09 | C 50.96<br>H 4.33<br>N 23.31 |
| $CH_3-\bigcirc-$ | $CH_3$ | 226–227(d) | | |
| $CH_3O-\bigcirc-$ | $CH_3$ | 176–178(d) | C 58.32<br>H 5.59<br>N 19.43 | C 58.01<br>H 5.60<br>C 19.23 |
| $Cl-\bigcirc-$ | $CH_3$ | 234–236(d) | C 53.34<br>H 4.48<br>N 19.14 | C 52.95<br>H 4.42<br>N 18.99 |

TABLE II-continued

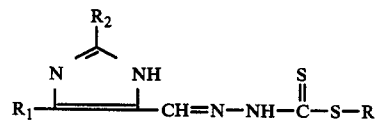

| $R_2$ | $R_1$ | m.p.(° C) | Analysis Calculated | Found |
|---|---|---|---|---|
| 2-methylphenyl | CH$_3$ | 160–162(d) | | |
| 2-naphthyl | CH$_3$ | >170(d) | | |
| C$_4$H$_9$— | CH$_3$ | 189.5–190.5(d) | C 55.44<br>H 7.61<br>N 23.52 | C 55.09<br>H 7.71<br>N 23.54 |
| C$_6$H$_{13}$— | CH$_3$ | 164–165(d) | C 58.62<br>H 8.33<br>N 21.04 | C 58.34<br>H 7.78<br>N 20.83 |
| cyclopropyl | CH$_3$ | 184–186(d) | C 54.04<br>H 6.35<br>N 25.21 | C 54.25<br>H 6.49<br>N 25.33 |
| cyclobutyl | CH$_3$ | 196–197(d) | | |
| cyclohexyl | CH$_3$ | 193–194(d) | C 59.07<br>H 7.63<br>N 21.20 | C 58.62<br>H 7.61<br>N 20.80 |
| Cl-phenyl · H$_2$O | Cl | 147–148 | C 43.5<br>H 3.63<br>N 16.9<br>Cl 21.14 | C 45.04<br>H 4.05<br>N 16.09<br>Cl 20.73 |

We claim:

1. A compound selected from the group consisting of those of the formula:

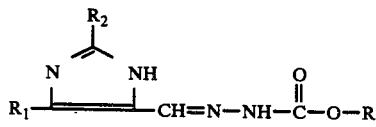

wherein R is alkyl having up to 3 carbon atoms; R$_1$ is hydrogen, chloro, bromo or alkyl having up to 3 carbon atoms; and R$_2$ is hydrogen, alkyl having up to 6 carbon atoms, methoxymethyl, phenyl, naphthyl, benzyl, or monosubstituted phenyl, wherein the latter monosubstituted substituent is alkyl (C$_1$-C$_3$), alkoxy (C$_1$-C$_3$), halo or nitro; and the tautomers thereof.

2. The compound according to claim 1 wherein R, R$_1$, and R$_2$ are methyl.

3. The compound according to claim 1 wherein R is ethyl, R$_1$ is isopropyl, and R$_2$ is isobutyl.

4. The compound according to claim 1 wherein R is n-propyl, R$_1$ is chloro, and R$_2$ is phenyl.

5. The compound according to claim 1 wherein R is ethyl, R$_1$ is methyl, and R$_2$ is phenyl.

6. A compound selected from the group consisting of those of the formula:

$$\underset{R_1}{\overset{R_2}{\underset{|}{\text{N}}\underset{\parallel}{=}\text{NH}}} \text{—CH=N—NH—}\overset{S}{\underset{\parallel}{\text{C}}}\text{—S—R}$$

wherein R is alkyl having up to 3 carbon atoms; R$_1$ is hydrogen, chloro, bromo or alkyl having up to 3 carbon atoms; and R$_2$ is hydrogen, alkyl having up to 6 carbon atoms, methoxymethyl, phenyl, naphthyl, benzyl or monosubstituted phenyl, wherein the latter monosubstituted substituent is alkyl (C$_1$-C$_3$), alkoxy (C$_1$-C$_3$), halo or nitro; and the tautomers thereof.

7. The compound according to claim 6 wherein R, R$_1$, and R$_2$ are ethyl.

8. The compound according to claim 6 wherein R is ethyl, R$_1$ is isopropyl, and R$_2$ is isobutyl.

9. The compound according to claim 6 wherein R is isopropyl, R$_1$ is chloro, and R$_2$ is phenyl.

10. The compound according to claim 6 wherein R is methyl, R$_1$ is hydrogen, and R$_2$ is phenyl.

* * * * *